(12) United States Patent
Forthmann et al.

(10) Patent No.: US 8,401,144 B2
(45) Date of Patent: Mar. 19, 2013

(54) METHOD AND APPARATUS FOR CORRECTING ARTIFACTS IN CIRCULAR CT SCANS

(75) Inventors: Peter Forthmann, Sandesneben (DE); Axel Thran, Hamburg (DE); Claas Bontus, Hamburg (DE); Roland Proksa, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 227 days.

(21) Appl. No.: 12/535,231

(22) Filed: Aug. 4, 2009

(65) Prior Publication Data

US 2010/0034342 A1  Feb. 11, 2010

Related U.S. Application Data

(60) Provisional application No. 61/086,831, filed on Aug. 7, 2008.

(51) Int. Cl.
*G01N 23/083* (2006.01)
*H05G 1/60* (2006.01)

(52) U.S. Cl. .................. 378/19; 378/98.8; 378/98.12

(58) Field of Classification Search .............. 378/4–20, 378/91, 98, 98.8, 98.12, 210
See application file for complete search history.

(56) References Cited

U.S. PATENT DOCUMENTS

| | | | | |
|---|---|---|---|---|
| 4,645,933 | A * | 2/1987 | Gambini et al. | 250/363.05 |
| 5,828,718 | A * | 10/1998 | Ruth et al. | 378/19 |
| 6,014,419 | A | 1/2000 | Hu | |
| 6,442,228 | B1 | 8/2002 | Woloschek et al. | |
| 7,113,569 | B2 * | 9/2006 | Okumura et al. | 378/150 |
| 7,305,063 | B2 * | 12/2007 | Heuscher | 378/12 |
| 7,359,477 | B2 | 4/2008 | Lauritsch et al. | |
| 2002/0131544 | A1 | 9/2002 | Aradate et al. | |
| 2003/0073893 | A1 * | 4/2003 | Hsieh | 600/407 |
| 2005/0100126 | A1 | 5/2005 | Mistretta et al. | |
| 2007/0253528 | A1 * | 11/2007 | Ning et al. | 378/15 |
| 2008/0095301 | A1 * | 4/2008 | Kohler et al. | 378/4 |
| 2009/0116717 | A1 * | 5/2009 | Kohler et al. | 382/131 |

FOREIGN PATENT DOCUMENTS

| | | |
|---|---|---|
| WO | 2005023114 A2 | 3/2005 |
| WO | 2007046036 A1 | 4/2007 |
| WO | 2007/113704 A1 | 10/2007 |
| WO | 2007119124 A1 | 10/2007 |
| WO | 2008042564 A1 | 4/2008 |
| WO | 2008047308 A1 | 4/2008 |

* cited by examiner

*Primary Examiner* — Anastasia Midkiff

(57) ABSTRACT

A scanning method and apparatus useful for correcting artifacts which may appear in a primary short circular CT scan are provided. A secondary helical scan performed on a stationary subject, or a secondary circular scan, may be used to correct for artifacts. The secondary scan may be performed with a smaller radiation dosage than the primary circular CT scan.

38 Claims, 4 Drawing Sheets

METHOD AND APPARATUS FOR CORRECTING ARTIFACTS IN CIRCULAR CT SCANS

CROSS REFERENCE TO RELATED APPLICATIONS

This application claims the benefit of U.S. provisional application Ser. No. 61/086,831 filed Aug. 7, 2008, which is incorporated herein by reference.

The present application relates generally to the imaging arts and more particularly to a scanning method and apparatus useful in computer tomography (CT) imaging. The method and apparatus provide for correcting cone-beam artifacts which may appear in circular CT scans. The scanning method and apparatus will thus be described with particular reference to CT imaging, but they may also find application in PET and SPECT imaging, and in other fields.

Computed Tomography (CT) is an imaging modality used in many different contexts, including medical imaging. In CT, an x-ray source disposed externally to an imaged subject produces x-rays which pass through the subject to be harnessed by an x-ray detector disposed approximately on the opposite side of the subject from the x-ray source. The x-ray source and x-ray detector are often rotated together around the imaged subject to record two dimensional x-ray images at different positions or projections around a central axis. The x-ray detector typically interacts with x-rays emitted by the x-ray source to produce electronic signals representative of the x-ray spectrum received by the detector, corresponding to a two dimensional x-ray projection image. The electronic signals representing several such two-dimensional x-ray projections may then be electronically processed to produce a CT image or other three dimensional x-ray based imaged of the subject.

A given x-ray detector has a "field of view", which is a measure of how many x-rays may be recorded by the x-ray detector in one reading. In most CT systems, a larger field of view is preferred to a smaller field of view, because that increases the usefulness and versatility of the system. However, there are technical and commercial challenges to building an x-ray detector with a large field of view in a cost-effective manner. Nevertheless, as this technology has developed over the course of time, commercially useful x-ray detectors have been designed using ever larger fields of view.

A representative CT imaging system 100 is shown in FIGS. 1 and 2. The CT imaging system 100 includes a subject support 110, such as a table or couch, which supports and positions a subject being imaged such as a patient. The CT imaging system 100 includes a stationary gantry 120 with a rotating gantry 130 mounted inside. The subject support 110 is linearly movable along the z-axis to allow the subject support 110 to extend into a bore 115 in the stationary gantry 120 for imaging. To perform an imaging scan, the rotating gantry 130 rotates inside the stationary gantry 120, around the z-axis. The z-axis is not, however, necessarily the center of rotation. One or more x-ray sources 140 mounted on the rotating gantry 130 produce an x-ray beam directed through the patient in the bore 115 to be detected by one or more x-ray detectors 150 in an array. One aspect of the x-ray detector array's field of view is the detector's width $W_D$ along the z-axis, which is best illustrated in FIG. 2.

The extent of the region(s) to be imaged in the patient along the z-axis may be larger than the width $W_D$ of the detector 150. For example, it may be desirable to obtain a CT image of a person's leg, when the width $W_D$ is only about 8 centimeters. In such situations, in order to completely cover the region(s) to be imaged, the subject support 110 may move the patient along the z-axis during the imaging. Such movement permits the entire region(s) of the patient to be imaged to be properly placed at the correct position in the bore 115 of the stationary gantry 120, relative to the x-ray source 140 and x-ray detector 150. The circular movement of the x-ray source 140 and x-ray detector 150 around the z-axis, combined with the relative lateral movement of the subject support 110 along the z-axis, can be idealized as a helical movement of the source 140 and detector 150 around a patient. Thus, these scans are often referred to as "helical" scans.

As the width $W_D$ of commercially available x-ray detectors 150 has increased over time, relative lateral movement of the patient P along the z-axis to perform a complete imaging operation has become less necessary. A representative example is cardiac CT imaging. For many years, the width $W_D$ of x-ray detectors 150 used in cardiac imaging was smaller than the width of a patient's heart along the z-axis, requiring patient movement to complete a cardiac scan. More recently, however, cardiac CT imaging systems have employed larger x-ray detectors 150 having a width $W_D$ which is greater than the width of a patient's heart along the z-axis. These larger x-ray detectors 150 can generate a complete CT image from one scan, without having to move the patient along the z-axis. The circular rotation of the x-ray source 140 and x-ray detector 150 around the z-axis, with a stationary subject support 110, can be idealized as movement along a circular arc in a single plane around the patient P. (Of course, as three dimensional objects, neither the source 140 nor the detector 150 is entirely disposed in a single two dimensional plane, but their rotational movement around a patient may be so idealized.) Thus, these scans are often referred to as "circular" or "planar" scans.

Such circular or planar scans have advantages and disadvantages. On the plus side, circular scans provide good temporal resolution. That is, circular scans can typically be completed in a shorter time relative to helical scans, in part because the patient need not be moved. This is advantageous, for example, in cardiac CT imaging. A typical human heart beats about 60 to 100 times per minute, which is about 1 to 1.6 beats per second. The beating movement of the heart during a CT imaging scan can give rise to motion artifacts in the resulting CT image. A circular CT scan can take much less than 1 second (i.e. much less than one heartbeat) to complete, and still generate sufficient imaging data for high quality CT image reconstruction. A helical CT scan, on the other hand, typically requires on the order of 1 to 3 seconds (i.e. more than 1 heartbeat) to complete. Thus, motion blur in the resulting CT images is minimized using a circular scan rather than a helical scan.

On the down side, however, circular or planar scans are inherently incomplete because imaging from only a single plane limits the amount of data available for the image reconstruction. This can result in undesirable cone-beam artifacts appearing in the resulting CT image.

Another source of general concern in CT and other kinds of imaging is the radiation dose applied to the patient. Generally, it is desirable to reduce the amount of x-ray radiation or other kind(s) of radiation administered to patients in order to complete the imaging process.

According to one aspect of the present invention, a principal circular imaging scan is combined with one or more secondary helical imaging scans to form an image. According to another aspect of the present invention, a principal circular imaging scan is combined with one or more secondary circular scans in different planes to form an image. The radiation dose applied during the secondary scan(s) may be less than the radiation dose applied during the principal scan.

One advantage to these methods is to increase the temporal resolution of the imaging scan, while reducing the amount of radiation administered to the patient. Numerous additional advantages and benefits will become apparent to those of ordinary skill in the art upon reading the following detailed description of preferred embodiments. The invention may take form in various components and arrangements of components, and in various process operations and arrangements of process operations. The drawings are only for the purpose of illustrating preferred embodiments and are not to be construed as limiting the invention.

Figure 1:
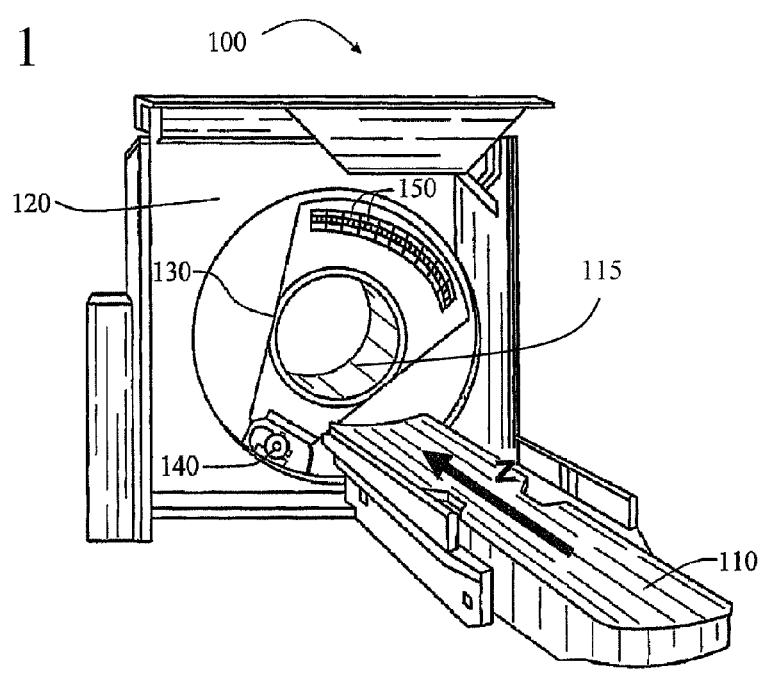
FIG. 1 is a perspective view of a CT imaging system 100.
Figure 2:
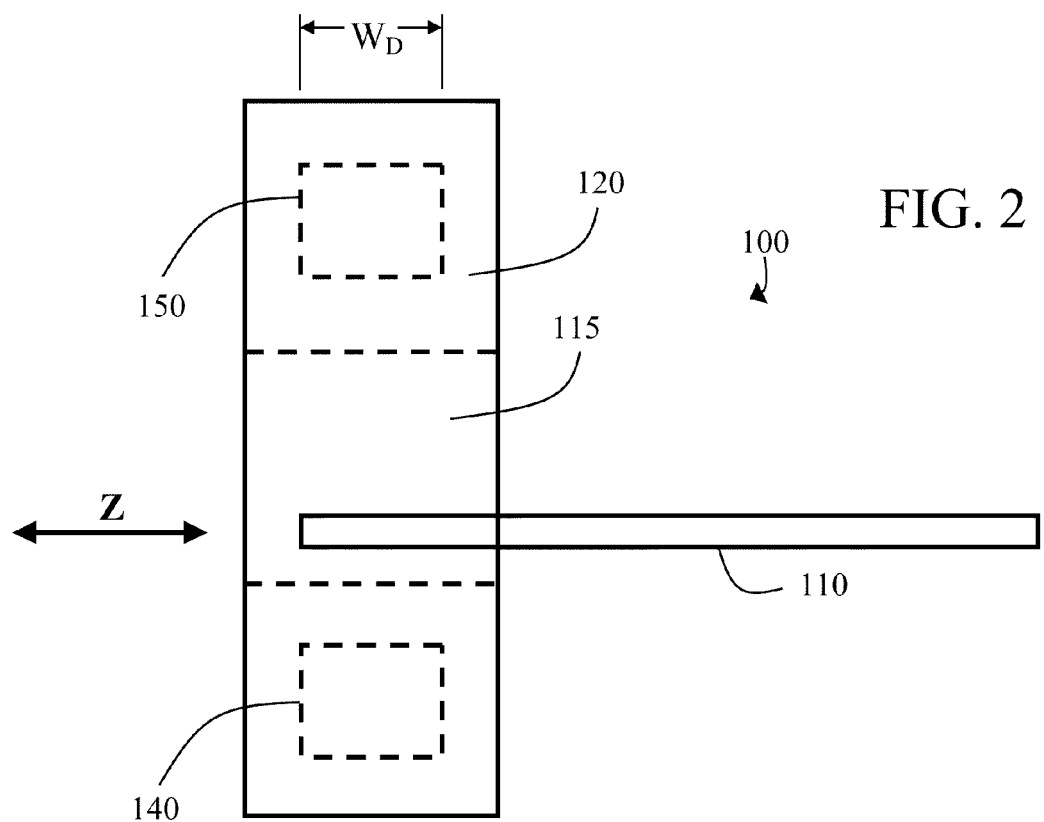
FIG. 2 is a schematic side view of the CT imaging system 100 of FIG. 1.

The methods described herein may be performed using the basic components of the CT imaging apparatus 100 described above in connection with FIGS. 1 and 2, so reference is made thereto as appropriate.

Figure 3:
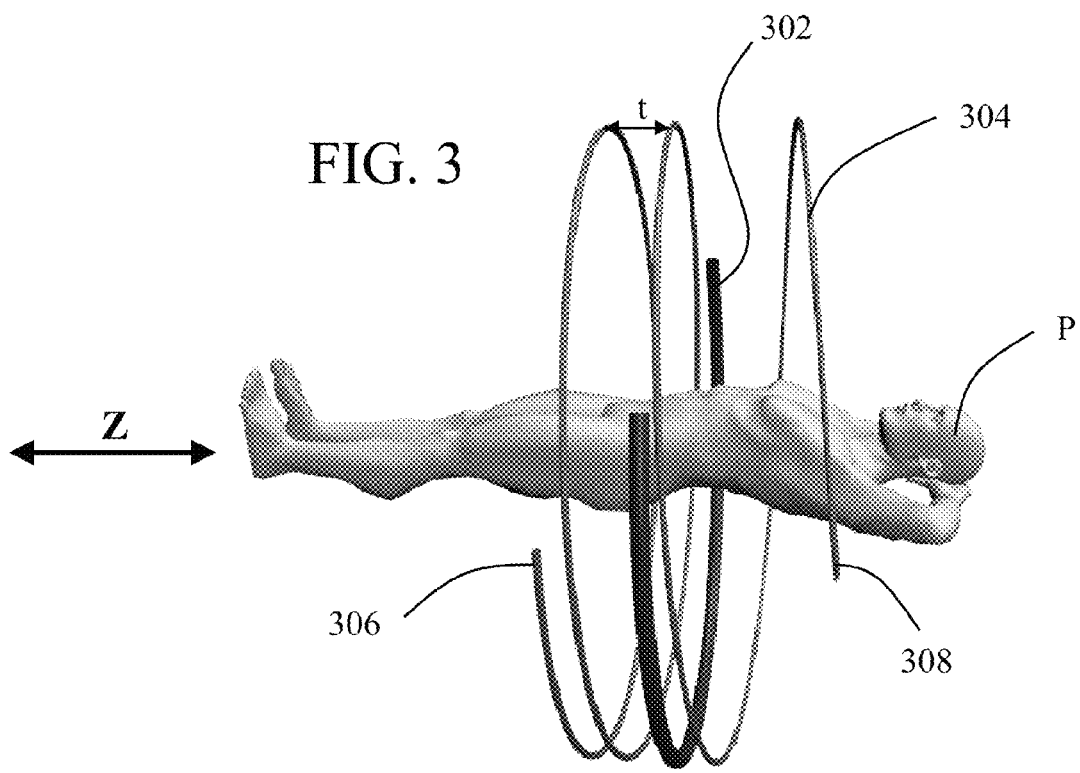
FIG. 3 is an illustration of a principal circular short scan combined with a secondary helical scan.

FIG. 3 illustrates a first method of performing an imaging scan of a patient, pursuant to which a principal circular scan is combined with one or more secondary helical scans to correct for cone-beam artifacts. The principal circular scan arc 302 and the secondary helical scan arc 304 illustrated in FIG. 3 represent the relative movement between the x-ray source 140 and/or detector 150, and the patient P, during the respective imaging scans. The table 110 which supports the patient P during this process is not shown in FIG. 3. Although the following description of the first method refers to one secondary helical scan 304, any number of such scans may be used, including two or more.

Thus, during the principal circular scan 302, the table 110 and the patient P on the table 110 remain stationary, and do not move along the z-axis. The x-ray source 140 and the x-ray detector 150 also do not move along the z-axis during this circular scan 302. As a result, the arc of the scan 302 lies along a circular path disposed in a plane which is perpendicular to the z-axis. In general, such circular scans may be characterized by the "included angle", which is the angular extent of the circular scan around the z-axis. The included angle of the principal circular scan 302 should be sufficiently large so that the x-ray detector 150 can gather enough data for a high quality image reconstruction as a result of the principal circular scan 302. In many cases, the included angle may be "short"—that is, less than 360°. For example, as illustrated in FIG. 3, the included angle may be 180° plus the fan angle of the x-ray source 140. Smaller included angles are usually preferred to larger included angles, due to the shorter time required for making the imaging scan. However, full circular scans may be employed as well.

During the secondary helical scan 304, as in the principal circular scan 302, the table 110 and the patient P on the table 110 remain stationary and do not move along the z-axis. However, unlike in the principal circular scan 302, one or both of the x-ray source 140 and the x-ray detector 150 do move along the z-axis during this helical scan 304. Such movement may be obtained in many ways. For example, the x-ray source 140 may be slidably mounted on a rail and controlled by a motor and gear arrangement. To perform the secondary helical scan 304, the source 140 may move to the starting position 306 of the scan and move axially along the z-axis to the ending position 308 of the scan. During that movement, the x-ray detector 150 may remain stationary or it may move with the x-ray source 140 along the z-axis. Moving the source 140 and/or detector 150 to perform the helical scan 304, instead of the patient P and table 110, provides a faster and easier data acquisition process.

As a result of the movement of the source 140 and/or detector 150, the arc of the scan 304 proceeds along a helical path relative to the patient P, from a starting point 306 to an ending point 308. The axial distance between the start 306 and end 308 of the helix, as well as the pitch "t" of the helix, have been exaggerated as shown in FIG. 3 for purposes of illustration. The pitch "t" of the secondary helical scan 304 may remain constant, or it may vary, during the secondary helical scan 304. Thus, as shown in FIG. 3, the pitch "t" may for example constantly accelerate from an initial value to a final value which is greater than the initial value. Although not shown, the pitch "t" may just as well constantly decrease during the secondary helical scan 304, or inconstantly increase or decrease, or vary by both increasing and decreasing during the scan 304.

The arc of FIG. 3 corresponding to the principal circular scan 302 is illustrated as being thicker than the arc corresponding to the secondary helical scan 304. That difference represents that the x-ray dosage applied by the x-ray source 140 to perform the principal circular scan 302 may be higher than the dosage applied during the secondary helical scan 304. That is because data from the principal helical scan 302 is used to create a high quality CT image reconstruction of the region(s) of interest within the patient P, such as the patient's heart. The data from the secondary helical scan 304, by contrast, is used principally to correct for cone-beam artifacts resulting in the CT image produced by the principal circular scan 302. A relatively low x-ray dosage is usually sufficient for that purpose, perhaps as low as just five percent of the principal scan dosage. Although the lower dosage causes a higher amount of noise in the image data, median filtering can compensate for the noise. Such filtering loses fine detail in soft tissue regions of the imaging data, but the result is good enough to correct the principal imaging data for cone-beam artifacts.

Once both the principal circular scan 302 and the secondary helical scan 304 have been completed, the data gathered by the two scans is processed to form a CT image. The data from the principal circular scan 302 is sufficient to generate such an image, but because of the planar geometry of the scan the data set is incomplete, so some cone-beam artifacts may result. The data from the secondary helical scan 304 may be used to correct for the cone-beam artifacts resulting from the principal circular scan 302, using conventional methods.

Figure 4:
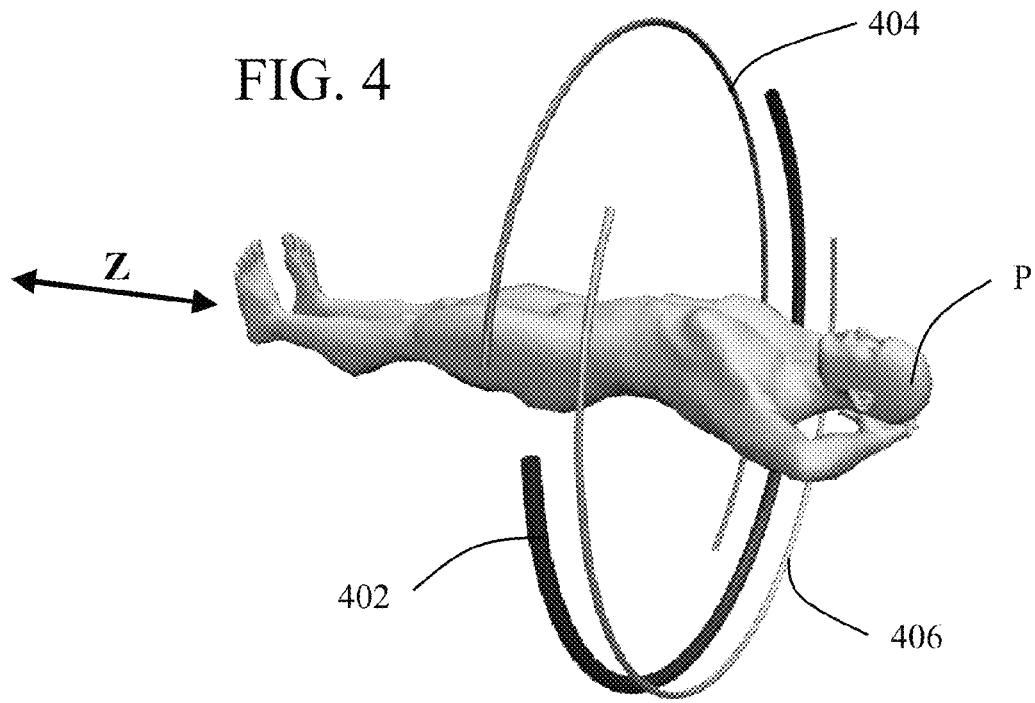
FIG. 4 is an illustration of a principal circular short scan combined with two secondary circular short scans.

FIG. 4 illustrates a second method of performing an imaging scan of a patient, pursuant to which a principal circular scan is combined with one or more secondary circular scans to correct for cone-beam artifacts. The principal circular scan arc 402 and the secondary circular scan arcs 404 and 406 illustrated in FIG. 4 represent the relative movement between the x-ray source 140 and/or detector 150, and the patient P, during the respective imaging scans. The 110 which supports the patient P during this process is not shown in FIG. 4. Although the following description of the second method refers to two secondary circular scans 404 and 406, any number of such scans may be used, including one such scan.

The principal circular scan 402 in this second method is substantially the same as the principal circular scan 302 of the first method illustrated in FIG. 3, and so will not be described further here.

During each secondary circular scan 404 and 406, as in the principal circular scan 402, the table 110 and the patient P on the table 110 remain stationary and do not move along the z-axis. However, the secondary circular scans 404 and 406 are each respectively taken in a plane perpendicular to the z-axis which is different from the plane of the primary circular scan 402 and from the plane of the other secondary circular scan. Preferably, at least one secondary circular scan is taken on each side of the principal circular scan 402.

Such axial displacement of the circular scans may be obtained in many ways. For example, the table 110 may move to position the patient P in the correct position for imaging by the x-ray source 140 and the x-ray detector 150. Standard step-and-shoot protocols may be employed to automate such table 110 movement during image acquisition. Thus, in connection with the second method illustrated in FIG. 4, the x-ray source 140 and x-ray detector 150 need not be translatable along the z-axis. Alternatively, of course, the x-ray source 140 and x-ray detector 150 may be translatable along the z-axis to take circular scans in different planes relative to a stationary patient P.

The included angle of the secondary circular scans 404 and 406 should be sufficiently large so that the x-ray detector 150 can gather enough data for correction of the principal circular scan 402, as discussed further below. In many cases, the included angle of the secondary circular scans 404 and 406 may be short. For example, as illustrated in FIG. 4, the included angle may be 180° plus the fan angle of the x-ray source 140. Smaller included angles are usually preferred to larger included angles, due to the shorter time required for making the imaging scan. However, full circular scans may be employed as well.

The arc of FIG. 4 corresponding to the principal circular scan 402 is illustrated as being thicker than the arcs corresponding to the secondary circular scans 404 and 406. That difference represents that the x-ray dosage applied by the x-ray source 140 to perform the principal circular scan 402 may be higher than the dosage applied during the secondary circular scans 404 and 406. That is because data from the principal circular scan 402 is used to create a high quality CT image reconstruction of the region(s) of interest within the patient P, such as the patient's heart. The data from the secondary circular scans 404 and 406, by contrast, is used principally to correct for cone-beam artifacts resulting in the CT image produced by the principal circular scan 402. A relatively low x-ray dosage is usually sufficient for that purpose, perhaps as low as just five percent of the principal scan dosage. Although the lower dosage causes a higher amount of noise in the image data, median filtering can compensate for the noise. Such filtering loses fine detail in soft tissue regions of the imaging data, but the result is good enough to correct the principal imaging data for cone-beam artifacts.

Once both the principal circular scan 402 and the secondary circular scans 404 and 406 have been completed, the data gathered by the scans is processed to form a CT image. The data from the principal circular scan 402 is sufficient to generate such an image, but because of the planar geometry of the scan 402 the resulting data set is incomplete, so some cone-beam artifacts may result. The data from the secondary circular scans 404 and 406 may be used to correct for the cone-beam artifacts resulting from the principal circular scan 402, using conventional methods.

Figure 5:
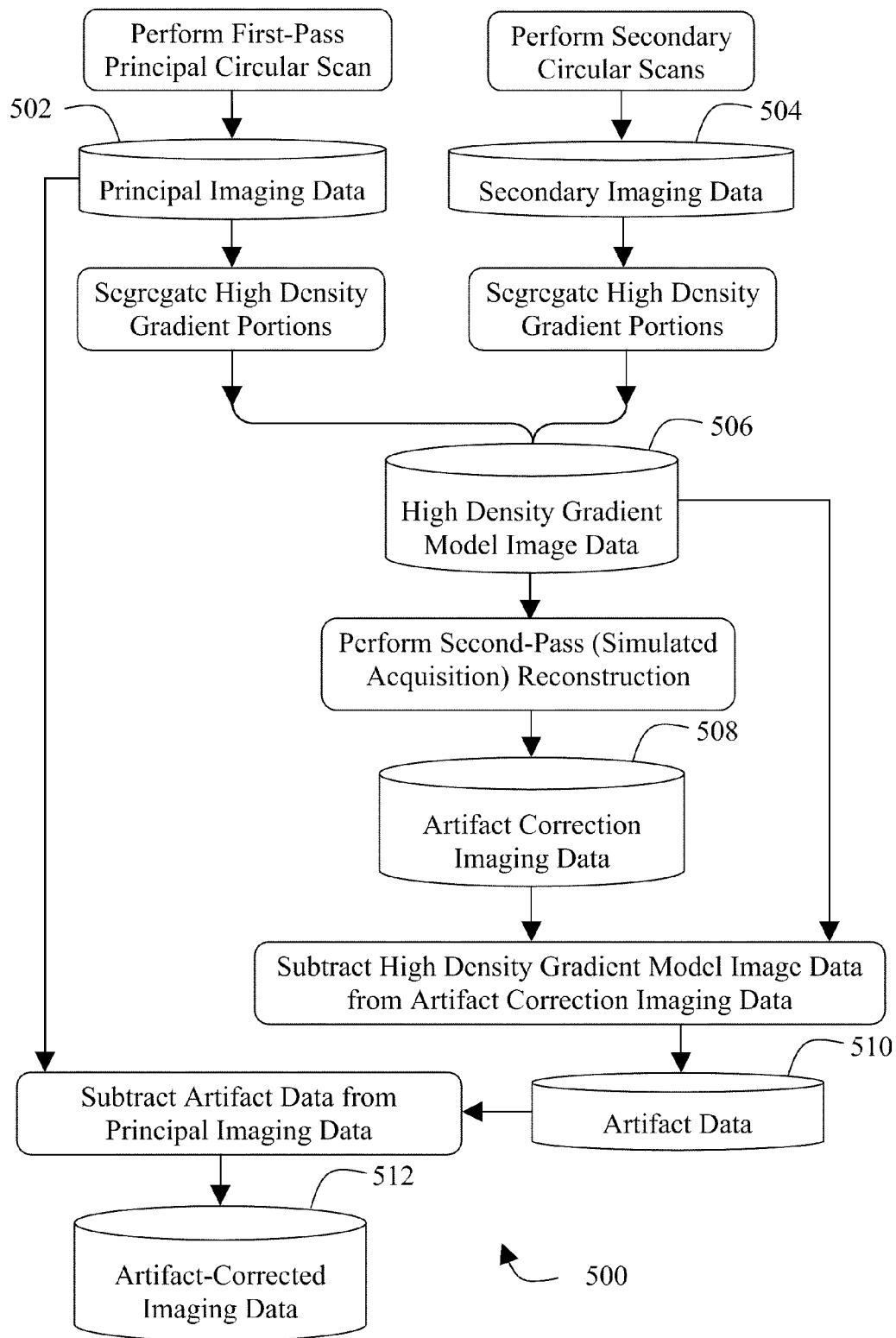
FIG. 5 illustrates an imaging process incorporating a second-pass cone-beam artifact correction.
Figure 6:
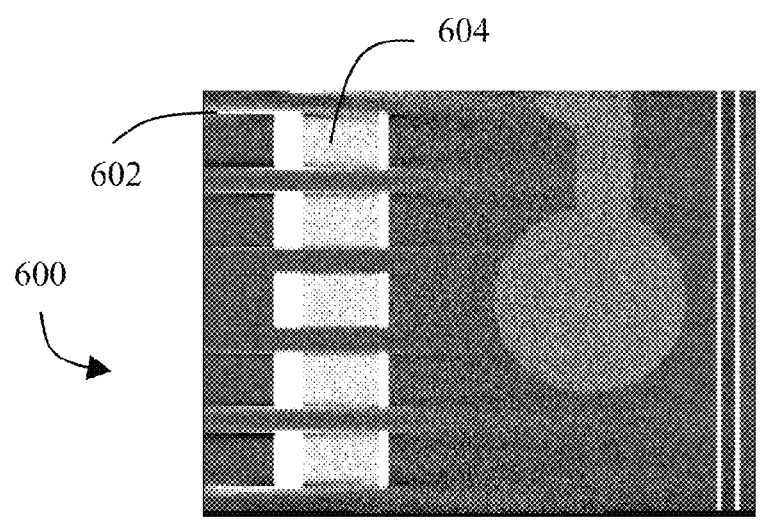
FIG. 6 is a reconstructed CT image without artifact correction.

FIG. 5 illustrates an imaging process 500 incorporating one such conventional method: a second-pass cone-beam artifact correction. According to the process, a first-pass principal circular scan 402 is performed to generate a principal imaging data set 502 for reconstruction as a CT image. FIG. 6 illustrates a reconstructed CT image 600 using only a principal imaging data set 502. The data set 502 and its resulting image 600 therefore contain undesirable cone-beam artifacts, such as seen at 602. High density gradients in the data set 502 and image 600, such as seen at 604, are responsible for the cone-beam artifacts 602 and generally do not contain very many cone-beam artifacts themselves. Thus, the principal imaging data set 502 corresponding to the image 600 is processed to segregate out the high density gradient portions such as 604. Those high density gradient portions are then used to create a high density gradient model image data set 506.

Figure 7:
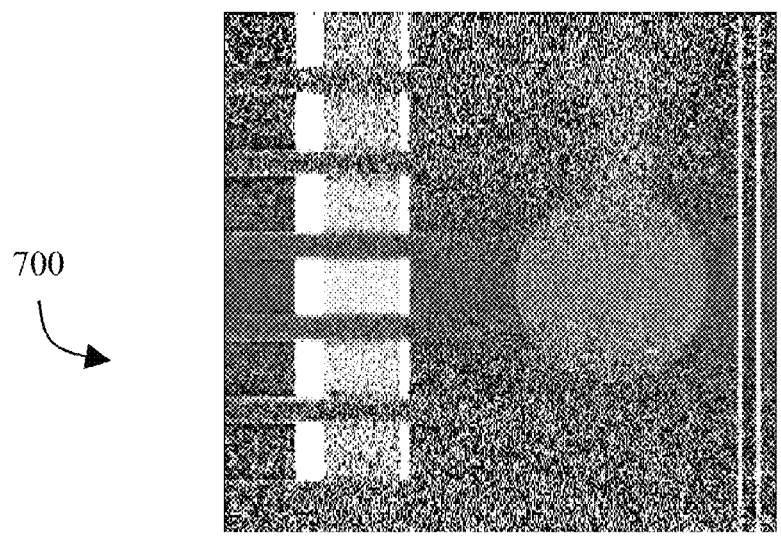
FIG. 7 is an image corresponding to a combination of a primary circular short scan and secondary circular short scans, used to correct the image of FIG. 6 for cone-beam artifacts.

In addition, secondary circular scans 404 and 406 are performed to generate a secondary imaging data set 504. In this particular application, the x-ray dosage applied during the secondary circular scans 404 and 406 may be approximately 5% of the total dosage applied during the principal circular scan 402. In addition, the secondary circular scans 404 and 406 may respectively be taken in planes offset from the principal circular scan 402 plane by about 100 mm to each side. The secondary imaging data set 504, like the principal imaging data set 502, is processed to segregate out the high density gradient portions. The high density gradient portions of the secondary imaging data set 504 are combined with the high density gradient portions of the principal imaging data set 502 to create the high density model image data set 506. FIG. 7 illustrates an image 700 combining a principal imaging data set 502 and a secondary imaging data set 504, before the high density gradient portions have been segregated.

The high density gradient model image data set 506 is then reconstructed in a simulated acquisition or second pass to generate an artifact correction imaging data set 508. Although the principal imaging data set 502 can alone be used for this purpose, the field of view available for the second-pass reconstruction in the z-axis direction is limited by the geometry of the x-ray source 104 and x-ray detector 150. Supplementing the principal data set 502 with the secondary imaging data set 504 advantageously increases the reconstructable field of view for the second-pass reconstruction.

In the event the patient P moves during the data acquisition, the principal imaging data set 502 can easily be registered with the secondary imaging data set 504. The images corresponding to the three scans 402, 404 and 406 overlap along the z-axis, so conventional rigid image registration methods can be applied for this purpose. For example, a weighted addition method may be applied.

Figure 8:
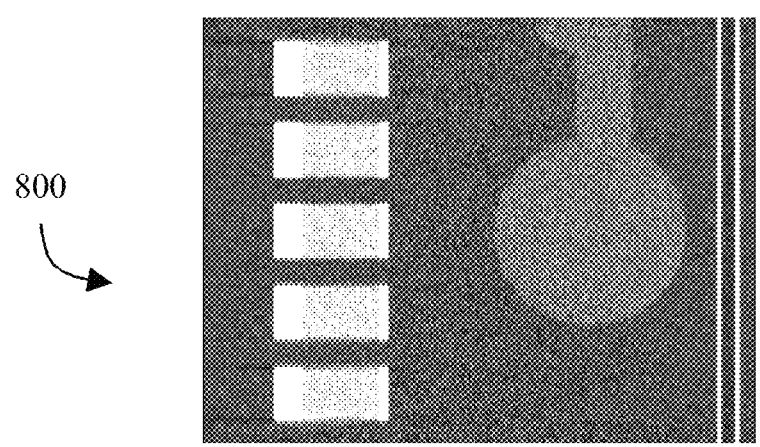
FIG. 8 is a reconstructed CT image with cone-beam artifact correction.

The high density gradient model image data set 506 is subtracted from the artifact correction imaging data set 508 to generate an artifact data set 510. The artifact data set 510 is representative of the artifacts appearing in the image 600 of the principal imaging data set 502. The artifact data set 510 is subtracted from the principal imaging data set 502 to produce an artifact-corrected data set 512. The artifact-corrected data set 512 is the artifact-corrected CT image. FIG. 8 shows such an artifact-corrected CT image 800, as can be appreciated by comparing FIG. 8 with FIG. 6 which contains artifacts.

The aforementioned functions can be performed as software logic. Thus, an image processor including an associated memory (not shown in the FIGURES) associated with the CT imaging system 100 can process electrical signals received from the x-ray detector 150 to form an x-ray based image of a subject according to a mathematical algorithm or algorithms. The image can be displayed on an associated display, and a user input such as a keyboard or mouse device may be provided for a user to control the image processor. The image processor may store related imaging data and other data in its associated memory.

"Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as the associated memory, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the associated memory. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Having thus described the preferred embodiments, the invention is now claimed to be:

1. A method of correcting an image of a patient containing artifacts, the method comprising:
    using a radiation source and a radiation detector to perform a primary circular scan, such that the primary circular scan generates a primary imaging data set;
    using the radiation source and the radiation detector to perform a secondary helical scan, such that the secondary helical scan generates a secondary imaging data set; and
    using the secondary imaging data set to correct the primary imaging data set for artifacts, and generate an image of the patient;
    wherein the radiation source or the radiation detector is translated axially along a z-axis during the secondary helical scan, while the patient remains substantially stationary in the z-axis direction; and
    wherein the radiation source applies a first radiation dosage during the primary circular scan, the radiation source applies a second radiation dosage during the secondary helical imaging scan, and the first radiation dosage is greater than the second radiation dosage.

2. The method of claim 1, wherein the radiation source is translated axially along the z-axis during the secondary helical scan, and the radiation detector remains substantially stationary in the z-axis direction during the secondary helical scan.

3. The method of claim 1, wherein the radiation source remains substantially stationary in the z-axis direction during the secondary helical scan, and the radiation detector is translated axially along the z-axis during the secondary helical scan.

4. A method of correcting an image of a patient containing artifacts, the method comprising:
    using a radiation source and a radiation detector to perform a primary circular scan, such that the primary circular scan generates a primary imaging data set;
    using the radiation source and the radiation detector to perform a secondary circular scan, such that the secondary circular scan generates a secondary imaging data set; and
    using the secondary imaging data set to correct the primary imaging data set for artifacts, and generate an image of the patient;
    wherein the primary circular scan is performed in a first plane substantially perpendicular to a z-axis, and the secondary circular scan is performed in a second plane substantially perpendicular to the z-axis which is different from the first plane.

5. The method of claim 4, further comprising using the radiation source and the radiation detector to perform a supplemental secondary circular scan in a third plane substantially perpendicular to the z-axis which is different from the first plane and the second plane, and using the supplemental secondary circular scan to generate the secondary imaging data set.

6. A method of correcting an image of a patient containing artifacts, the method comprising:
    using a radiation source and a radiation detector to perform a primary circular scan, such that the primary circular scan generates a primary imaging data set;
    using the radiation source and the radiation detector to perform a secondary circular scan, such that the secondary circular scan generates a secondary imaging data set; and
    using the secondary imaging data set to correct the primary imaging data set for artifacts, and generate an image of the patient;
    wherein the radiation source applies a first radiation dosage during the primary circular scan, the radiation source applies a second radiation dosage during the secondary circular imaging scan, and the first radiation dosage is greater than the second radiation dosage.

7. The method of claim 4, further comprising correcting the primary imaging data set for artifacts using a second-pass cone-beam artifact reconstruction.

8. An apparatus for correcting a CT image of a patient containing artifacts, the apparatus comprising:
    an x-ray source and an x-ray detector both configured to rotate around a z-axis; and a computer readable medium comprising logic to
perform a primary circular scan using the x-ray source and x-ray detector, such that the primary circular scan generates a primary imaging data set,
perform a secondary helical scan using the x-ray source and x-ray detector, such that the secondary helical scan generates a secondary imaging data set, and
use the secondary imaging data set to correct the primary imaging data set for artifacts, and generate an image of the patient;
wherein at least one of the x-ray source and the x-ray detector is configured to translate axially along a z-axis, and the computer readable medium further comprises logic to translate the radiation source or the radiation detector axially along the z-axis during the secondary helical scan, while the patient remains substantially stationary in the z-axis direction; and
wherein the computer readable medium further comprises logic to apply a first radiation dosage during the primary circular scan, and to apply a second radiation dosage during the secondary helical imaging scan, such that the first radiation dosage is greater than the second radiation dosage.

9. The apparatus of claim 8, wherein the radiation source is translated axially along the z-axis during the secondary helical scan, and the radiation detector remains substantially stationary in the z-axis direction during the secondary helical scan.

10. The apparatus of claim 8, wherein the radiation source remains substantially stationary in the z-axis direction during the secondary helical scan, and the radiation detector is translated axially along the z-axis during the secondary helical scan.

11. The apparatus of claim 8, wherein both the radiation source and the radiation detector are translated axially along the z-axis during the secondary helical scan.

12. An apparatus for correcting a CT image of a patient containing artifacts, the apparatus comprising:
an x-ray source and an x-ray detector both configured to rotate around a z-axis; and
a computer readable medium comprising logic to
perform a primary circular scan using the x-ray source and x-ray detector, such that the primary circular scan generates a primary imaging data set,
perform a secondary circular scan using the x-ray source and x-ray detector, such that the secondary circular scan generates a secondary imaging data set, and
use the secondary imaging data set to correct the primary imaging data set for artifacts, and generate an image of the patient;
wherein the primary circular scan is performed in a first plane substantially perpendicular to a z-axis, and the secondary circular scan is performed in a second plane substantially perpendicular to the z-axis which is different from the first plane.

13. An apparatus for correcting a CT image of a patient containing artifacts, the apparatus comprising:
an x-ray source and an x-ray detector both configured to rotate around a z-axis; and
a computer readable medium comprising logic to
perform a primary circular scan using the x-ray source and x-ray detector, such that the primary circular scan generates a primary imaging data set,
perform a secondary circular scan using the x-ray source and x-ray detector, such that the secondary circular scan generates a secondary imaging data set, and
use the secondary imaging data set to correct the primary imaging data set for artifacts, and generate an image of the patient;
wherein the computer readable medium further comprises logic to apply a first radiation dosage during the primary circular scan, and to apply a second radiation dosage during the secondary circular imaging scan, such that the first radiation dosage is greater than the second radiation dosage.

14. The method of claim 4, further comprising:
using the radiation source and the radiation detector to perform a third circular scan, such that the third circular scan generates a third imaging data set; and
using the third imaging data set to correct the primary imaging data set for artifacts, and generate an image of the patient.

15. The method of claim 14, wherein the third circular scan is performed in a third plane substantially perpendicular to the z-axis which is different from the first plane and from the second plane, wherein the second plane and the third plane are disposed on opposite sides of the first plane.

16. The method of claim 6, further comprising use of a median filter to compensate for noise in the secondary imaging data set.

17. The apparatus of claim 12, wherein the computer readable medium further comprises logic to:
perform a third circular scan using the x-ray source and x-ray detector, such that the third circular scan generates a third imaging data set, and
use the third imaging data set to correct the primary imaging data set for artifacts, and generate an image of the patient.

18. The apparatus of claim 17, wherein the third circular scan is performed in a third plane substantially perpendicular to the z-axis which is different from the first plane and from the second plane, wherein the second plane and the third plane are disposed on opposite sides of the first plane.

19. The apparatus of claim 14, wherein the computer readable medium further comprises logic to use a median filter to compensate for noise in the secondary imaging data set.

20. The method of claim 1, wherein the primary circular scan comprises an included angle of less than 360°.

21. The method of claim 20, wherein the primary circular scan is 180° plus a fan angle of the radiation source.

22. The method of claim 4, wherein at least one of the primary circular scan and the secondary circular scan comprises an included angle of less than 360°.

23. The method of claim 22, wherein the circular scan which comprises an included angle of less than 360° has an included angle which is 180° plus a fan angle of the radiation source.

24. The apparatus of claim 8, wherein the primary circular scan comprises an included angle of less than 360°.

25. The apparatus of claim 24, wherein the primary circular scan is 180° plus a fan angle of the x-ray source.

26. The apparatus of claim 12, wherein at least one of the primary circular scan and the secondary circular scan comprises an included angle of less than 360°.

27. The apparatus of claim 26, wherein the circular scan which comprises an included angle of less than 360° has an included angle which is 180° plus a fan angle of the radiation source.

28. The method of claim 1, wherein the artifacts comprise cone beam artifacts.

29. The method of claim 4, wherein the artifacts comprise cone beam artifacts.

30. The method of claim 6, wherein the artifacts comprise cone beam artifacts.

31. The method of claim 1, wherein the secondary helical scan comprises a pitch, and the method further comprises varying the pitch during the secondary helical scan.

32. The apparatus of claim 8, wherein the secondary helical scan comprises a pitch, and the computer readable medium further comprises logic to vary the pitch during the secondary helical scan.

33. The method of claim 6, further comprising using the radiation source and the radiation detector to perform a supplemental secondary circular scan, and using the supplemental secondary circular scan to generate the secondary imaging data set.

34. The method of claim 33, wherein the primary circular scan is performed in a first plane substantially perpendicular to a z-axis, the secondary circular scan is performed in a second plane substantially perpendicular to the z-axis which is different from the first plane, the third circular scan is performed in a third plane substantially perpendicular to the z-axis which is different from the first plane and from the second plane, and the second plane and the third plane are disposed on opposite sides of the first plane.

35. The apparatus of claim 13, wherein the computer readable medium further comprises logic to perform a supplemental secondary circular scan, and to use the supplemental secondary circular scan to generate the secondary imaging data set.

36. The apparatus of claim 35, wherein the primary circular scan is performed in a first plane substantially perpendicular to a z-axis, the secondary circular scan is performed in a second plane substantially perpendicular to the z-axis which is different from the first plane, the third circular scan is performed in a third plane substantially perpendicular to the z-axis which is different from the first plane and from the second plane, and the second plane and the third plane are disposed on opposite sides of the first plane.

37. The method of claim 6, wherein at least one of the primary circular scan and the secondary circular scan comprises an included angle of less than 360°.

38. The apparatus of claim 13, wherein at least one of the primary circular scan and the secondary circular scan comprises an included angle of less than 360°.

* * * * *